(12) United States Patent
Malyugin et al.

(10) Patent No.: US 9,974,688 B2
(45) Date of Patent: May 22, 2018

(54) METHOD OF IMPLANTING AN IRIS-EXPANDING DEVICE

(71) Applicants: MicroSurgical Technology, Inc., Redmond, WA (US); Boris Malyugin, Moscow (RU)

(72) Inventors: Boris Malyugin, Moscow (RU); Vaclav Dusek, Bellevue, WA (US); Lawrence Laks, Bellevue, WA (US)

(73) Assignee: Microsurgical Technology, Inc., Redmond, WA (US)

( * ) Notice: Subject to any disclaimer, the term of this patent is extended or adjusted under 35 U.S.C. 154(b) by 0 days. days.

(21) Appl. No.: 15/648,311

(22) Filed: Jul. 12, 2017

(65) Prior Publication Data

US 2017/0312126 A1 Nov. 2, 2017

Related U.S. Application Data

(63) Continuation of application No. 13/661,982, filed on Oct. 26, 2012, which is a continuation of application
(Continued)

(51) Int. Cl.
*A61F 9/007* (2006.01)
*A61B 17/02* (2006.01)
*A61F 9/00* (2006.01)

(52) U.S. Cl.
CPC ...... *A61F 9/00736* (2013.01); *A61B 17/0231* (2013.01); *A61F 9/0017* (2013.01)

(58) Field of Classification Search
CPC .......... A61F 2/1662; A61F 9/007; A61F 2/14; A61F 2220/0008; A61F 2250/0004; A61F 2250/0006; A61F 2250/0007; A61F 2250/001; A61F 2250/0059; A61F 2250/007; A61F 17/0231
(Continued)

(56) References Cited

U.S. PATENT DOCUMENTS 1,506,186 A 8/1924 Owen et al.
2,761,457 A 9/1956 Wood
(Continued)

FOREIGN PATENT DOCUMENTS

DE 93 20 127 U1 4/1994
RU 14506 U1 2/2000
(Continued)

OTHER PUBLICATIONS

Cimberle, M., "New Pupil Expander Easier to Implant, Gentle on the Iris," *Ocular Surgery News Europe Asia Edition*, [online], May 2006 [retrieved on Mar. 27, 2013]. Retrieved from the Internet URL: http://www.osnsupersite.com/view.aspx?rid=16863.
(Continued)

*Primary Examiner* — Paul Prebilic
(74) *Attorney, Agent, or Firm* — Hamilton, Brook, Smith & Reynolds, P.C.

(57) ABSTRACT

Methods of implanting an iris-expanding medical device in an eye. The methods can use an inserter which includes an inserter handle and a cannula attached to the inserter handle. Once inserted, the iris-expending medical device can maintain a pupil in an extended position during an ophthalmic procedure such as phacoemulsification.

11 Claims, 4 Drawing Sheets

Related U.S. Application Data

No. 12/074,742, filed on Mar. 5, 2008, now Pat. No. 8,323,296.

(60) Provisional application No. 60/918,405, filed on Mar. 15, 2007.

(58) Field of Classification Search
USPC .......................................................... 606/107
See application file for complete search history.

(56) References Cited

U.S. PATENT DOCUMENTS

| | | | |
|---|---|---|---|
| 3,975,779 A | | 8/1976 | Richards et al. |
| 4,203,168 A | | 5/1980 | Rainin et al. |
| 4,321,916 A | | 3/1982 | McKee |
| 4,387,706 A | | 6/1983 | Glass |
| 4,412,532 A | | 11/1983 | Anthony |
| 4,446,582 A | | 5/1984 | Hanna |
| 4,782,820 A | * | 11/1988 | Woods ............... A61B 17/0231 600/208 |
| 4,991,567 A | * | 2/1991 | McCuen, II ....... A61B 17/0231 600/204 |
| 5,163,419 A | | 11/1992 | Goldman |
| 5,267,553 A | * | 12/1993 | Graether ............ A61B 17/0231 600/236 |
| 5,299,564 A | | 4/1994 | Sabatino |
| 5,318,011 A | * | 6/1994 | Federman .......... A61B 17/0231 600/236 |
| 5,322,054 A | | 6/1994 | Graether |
| 5,334,217 A | | 8/1994 | Das |
| 5,374,272 A | | 12/1994 | Arpa et al. |
| 5,427,088 A | * | 6/1995 | Graether ............ A61B 17/0231 600/226 |
| 5,441,045 A | | 8/1995 | Federman |
| 5,456,274 A | | 10/1995 | Selbee et al. |
| 5,489,295 A | | 2/1996 | Piplani et al. |
| 5,634,884 A | * | 6/1997 | Graether ............ A61B 17/0231 600/210 |
| 5,693,085 A | | 12/1997 | Buirge et al. |
| 5,951,565 A | | 9/1999 | Freeman |
| 6,068,643 A | * | 5/2000 | Milverton .......... A61B 17/0231 606/107 |
| 6,200,336 B1 | * | 3/2001 | Pavcnik .................... A61F 2/07 623/1.13 |
| 6,231,583 B1 | | 5/2001 | Lee |
| 6,332,866 B1 | * | 12/2001 | Grieshaber ........ A61B 17/0231 600/210 |
| 6,497,724 B1 | | 12/2002 | Stevens et al. |
| 6,620,098 B1 | | 9/2003 | Milverton |
| 6,814,748 B1 | | 11/2004 | Baker et al. |
| 7,305,996 B2 | | 12/2007 | Kraft et al. |
| 7,412,993 B2 | | 8/2008 | Tzeng |
| 7,985,180 B2 | | 7/2011 | Brown |
| 8,257,256 B1 | | 9/2012 | Krolman |
| 8,323,296 B2 | | 12/2012 | Malyugin |
| 8,376,743 B1 | | 2/2013 | Bukhary |
| 8,496,583 B1 | | 7/2013 | Reynard |
| 8,900,136 B2 | | 12/2014 | Cote et al. |
| 9,089,397 B2 | | 7/2015 | Clarke |
| 9,504,459 B1 | | 11/2016 | Nallakrishnan |
| 9,763,653 B2 | | 9/2017 | Malyugin |
| 9,918,710 B2 | | 3/2018 | Malyugin et al. |
| 2002/0004676 A1 | | 1/2002 | Wallace |
| 2003/0092970 A1 | * | 5/2003 | Lee .................... A61B 17/0231 600/236 |
| 2008/0108879 A1 | | 5/2008 | Brown |
| 2008/0243139 A1 | * | 10/2008 | Dusek ................ A61B 17/0231 606/107 |
| 2008/0269888 A1 | | 10/2008 | Malyugin |
| 2008/0275461 A1 | | 11/2008 | Nallakrishnan |
| 2012/0136322 A1 | | 5/2012 | Alster et al. |
| 2012/0289786 A1 | * | 11/2012 | Dusek ................ A61B 17/0231 600/236 |
| 2013/0053860 A1 | | 2/2013 | Malyugin |
| 2013/0096386 A1 | | 4/2013 | Christensen et al. |
| 2013/0131458 A1 | | 5/2013 | Malugin et al. |
| 2013/0267988 A1 | | 10/2013 | Sussman et al. |
| 2013/0331939 A1 | | 12/2013 | Stevens |
| 2014/0221759 A1 | | 8/2014 | Mackool et al. |
| 2014/0378773 A1 | | 12/2014 | Dykes |
| 2015/0164685 A1 | | 6/2015 | Bhattacharjee |
| 2015/0265269 A1 | | 9/2015 | Malyugin |
| 2017/0312127 A1 | | 11/2017 | Malyugin et al. |

FOREIGN PATENT DOCUMENTS

| | | | | |
|---|---|---|---|---|
| RU | | 14505 U1 | 9/2000 | |
| WO | WO 95/15120 | | 6/1995 | |
| WO | WO 00/32141 | | 6/2000 | |
| WO | WO2008115454 A1 | * | 3/2008 | ......... A61B 17/0231 |
| WO | WO2008115455 A1 | * | 3/2008 | ......... A61F 17/0231 |

OTHER PUBLICATIONS

He et al, "Distribution and Heritability of Iris Thickness and Pupil Size in Chinese: The Guangzhou Twin Eye Study", Apr. 2009, IOVS ARVO Journal, vol. 50, Issue 4, pp. 1593-1597.

* cited by examiner

METHOD OF IMPLANTING AN IRIS-EXPANDING DEVICE

RELATED APPLICATIONS

This application is a continuation of U.S. application Ser. No. 13/661,982 filed Oct. 26, 2012, which is a continuation of U.S. application Ser. No. 12/074,742, filed Mar. 5, 2008, now U.S. Pat. No. 8,323,296 issued Dec. 4, 2012, which claims the benefit of U.S. Provisional Application No. 60/918,405 filed on Mar. 15, 2007.

The entire teachings of the above application(s) are incorporated herein by reference.

BACKGROUND OF THE INVENTION

Field of the Invention

The present invention relates to a ring used in a ophthalmic surgical procedure.

Background Information

There are various ophthalmic procedures that require the dilation of the pupil. For example, cataracteous lenses are typically replaced in a procedure commonly referred to as phacoemulsification or phaco for short. In a phaco procedure the lens is broken up with an instrument, typically with an ultrasonically driven tool. The instrument has an aspiration port that aspirates the broken lens material from the patient's ocular chamber.

It is desirable to extend the pupil during a phaco procedure to provide the surgeon with a wide view of the lens. One technique for extending the pupil includes pulling back the iris with a series of plastic hooks. It is has been found that using plastic hooks can cause damage to iris tissue.

SUMMARY OF THE INVENTION

A ring used to maintain a pupil in an extended position during an ophthalmic procedure. The ring has a plurality of loops.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Described is a ring that can maintain a pupil in an extended position during an ophthalmic procedure. The ring has a plurality of loops that capture iris tissue. The ring is configured to extend the pupil when iris tissue is inserted into each loop. An ophthalmic procedure such as phacoemulsification can then be performed on the patient. The ring has a center opening that provides a wide view of the ocular chamber during the procedure.

Figure 1:
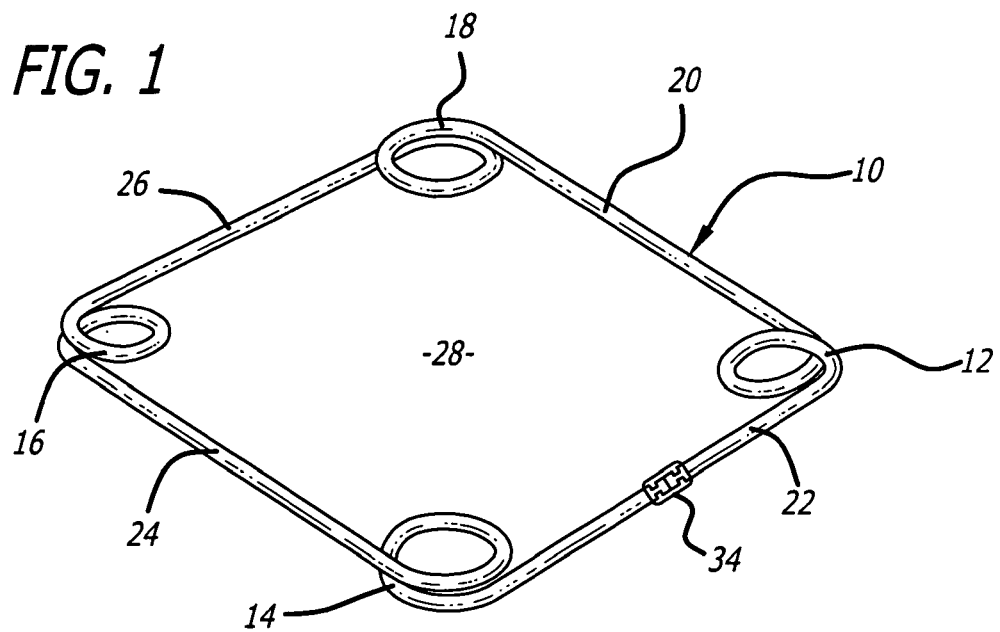
FIG. 1 is an illustration of a ring of the present invention.

Referring to the drawings more particularly by reference numbers, FIG. 1 shows an embodiment of a ring 10 that can be used to extend a pupil during an ophthalmic procedure. The ring 10 has a plurality of loops 12, 14, 16 and 18 located at the corners of four sides 20, 22, 24 and 26. Each loop 12, 14, 16 and 18 may be formed by one full turn. Although one full turn is shown and described, it is to be understood that each loop 12, 14, 16 and 18 may have multiple turns. The four sides 20, 22, 24 and 26 circumscribe a center opening 28.

The ring 10 preferably has a square configuration such that the sides 20, 22, 24 and 26 are of equal dimension. Although a square ring is shown and described, it is to be understood that the ring may have a rectangular configuration where all sides 20, 22, 24 and 26 are not of equal dimension. Additionally, the ring may have a nonrectangular shape. For example, the ring 10 may be shaped as a triangle that has three sides and three loops located at the ring corners. Although three and four sided rings have been described, it is to be understood that the ring may have any number of side and loops. The ring 10 is preferably constructed from a molded plastic material, although it is to be understood that other materials such as metal or plastic coated metal may be employed.

Figure 2:
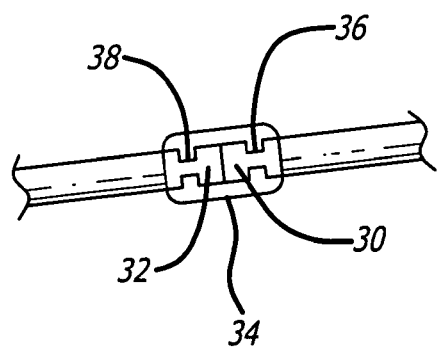
FIG. 2 is an illustration showing an enlarged view of the ring.

FIG. 2 shows a preferred embodiment for constructing the ring 10. One side 20 of the ring 10 has two ends 30 and 32 that are butt attached by an adhesive 34. Each end 30 and 32 may have an indent 36 and 38, respectively. The adhesive 34 can flow into the indents 36 and 38 to increase the strength of the butt attachment of the ring 10. The indents 36 and 38 create surface structure that minimizes shearing and delamination of the adhesive 34 from the ring 10. By way of example, the adhesive 34 may be a biocompatible material such as Class VI epoxy. The adhesive 34 can be applied with a tool (not shown) that insures a repeatable volume and dimensions of the solidified adhesive form.

Figure 3:
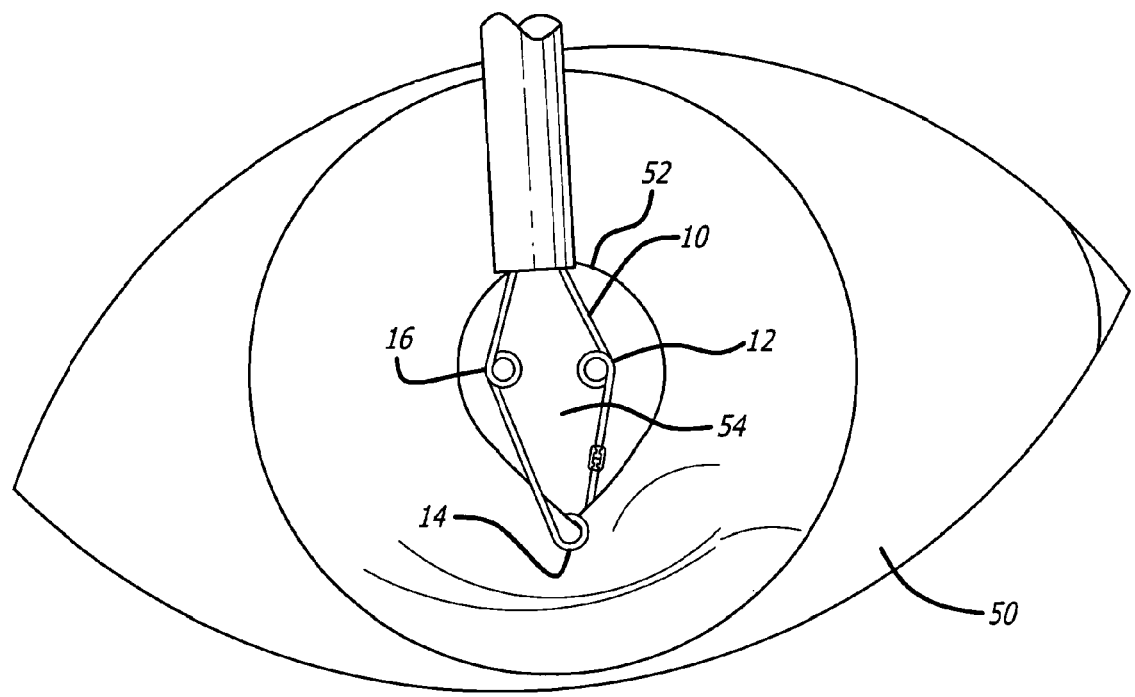
FIG. 3 is an illustration showing iris tissue being inserted into a first loop of the ring.
Figure 4:
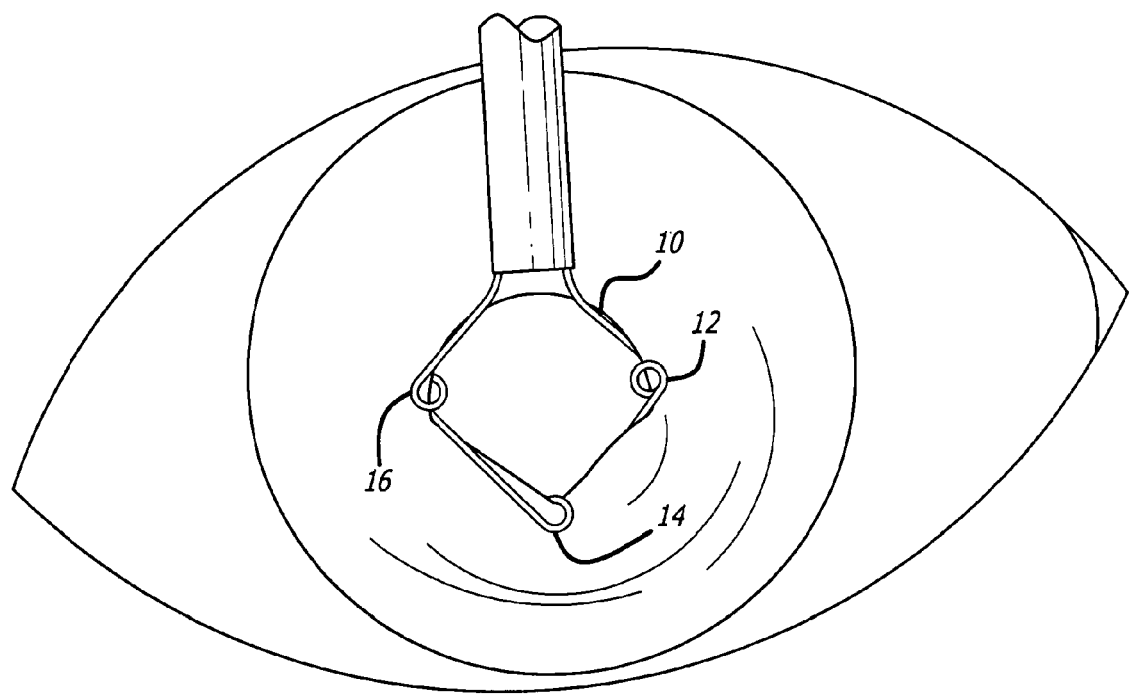
FIG. 4 is an illustration showing iris tissue being inserted into a second loop of the ring.

FIG. 3 shows the initial stages of the ring 10 being inserted into a patient's eye 50 to stretch the iris 52 and extend the pupil 54. A tool such as a forcep (not shown) can be used to pull the iris so that iris tissue is inserted into loop 14 of the ring 10. As shown in FIG. 4, the ring 10 can be manipulated so that iris tissue is inserted into loops 12 and 16.

Figure 5:
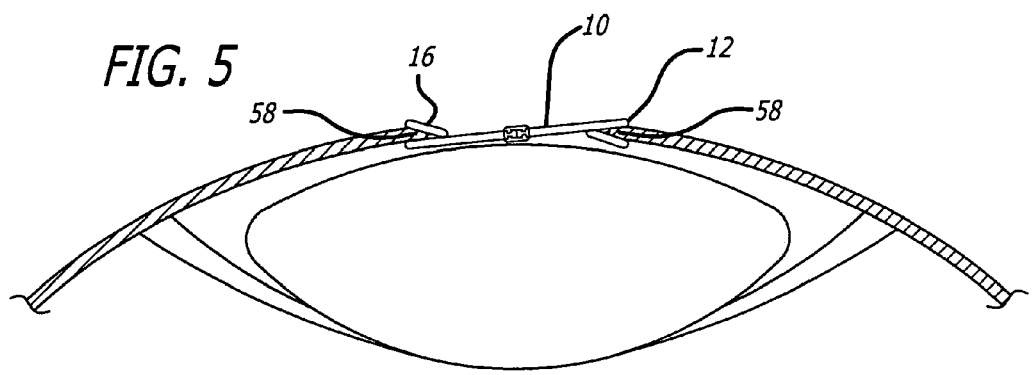
FIG. 5 is an illustration showing the iris tissue within gaps of the loops.

As shown in FIG. 1, an example of the device of the present invention is a polygonal ring formed from a single strand. As shown in FIG. 5 each loop 12, 16, etc. has a gap 58 that receives and captures iris tissue. The gap is wedge-shaped and faces the periphery of the ring 10. It is formed between a top portion of the strand and a bottom portion of the strand. The loop design provides an easy means of inserting and capturing iris tissue. The flexibility of the ring 10 allows the loops to deflect and apply a clamping force onto the iris tissue. The clamping force assist in maintaining the position of the ring relative to the eye.

Figure 6:
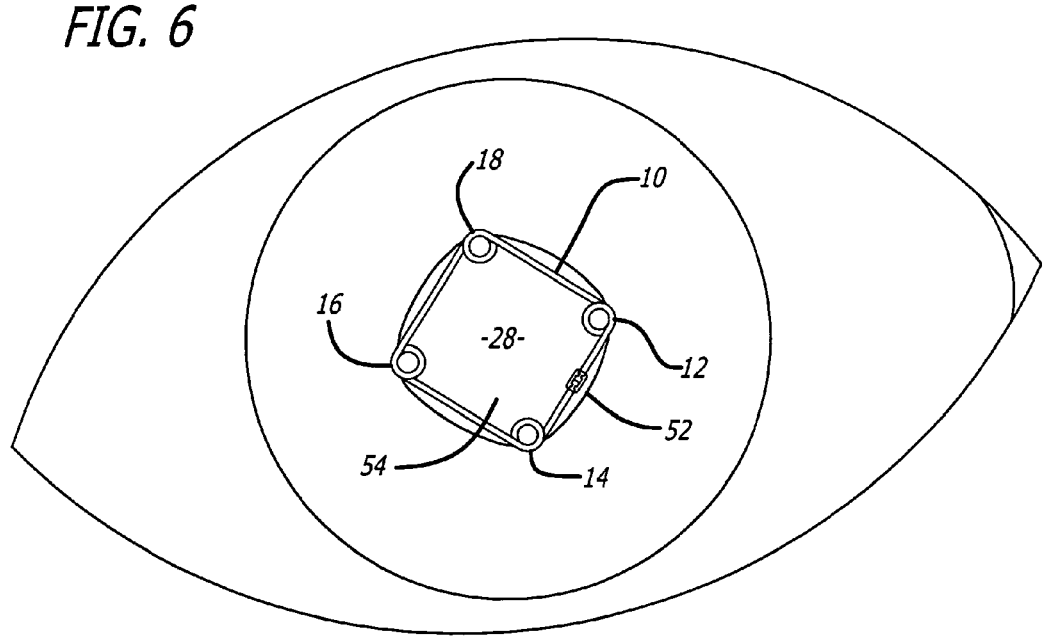
FIG. 6 is an illustration showing a pupil being maintained in an extended position by the ring.

As shown in FIG. 6 iris tissue can be inserted into the second 14 and fourth 18 loops to fully stretch the iris 52 and extend the pupil 54. An ophthalmic procedure can then be performed on the eye. For example, a phaco procedure can be performed wherein the lens is emulsified and aspirated from the eye. The ring 10 maintains the pupil 54 in the fully extended position while the center opening 28 provides a wide viewing area during the procedure. When the procedure is complete one of the sides 20, 22, 24 or 26 can be cut with an instrument and the ring 10 can be removed from the eye.

Figure 7:
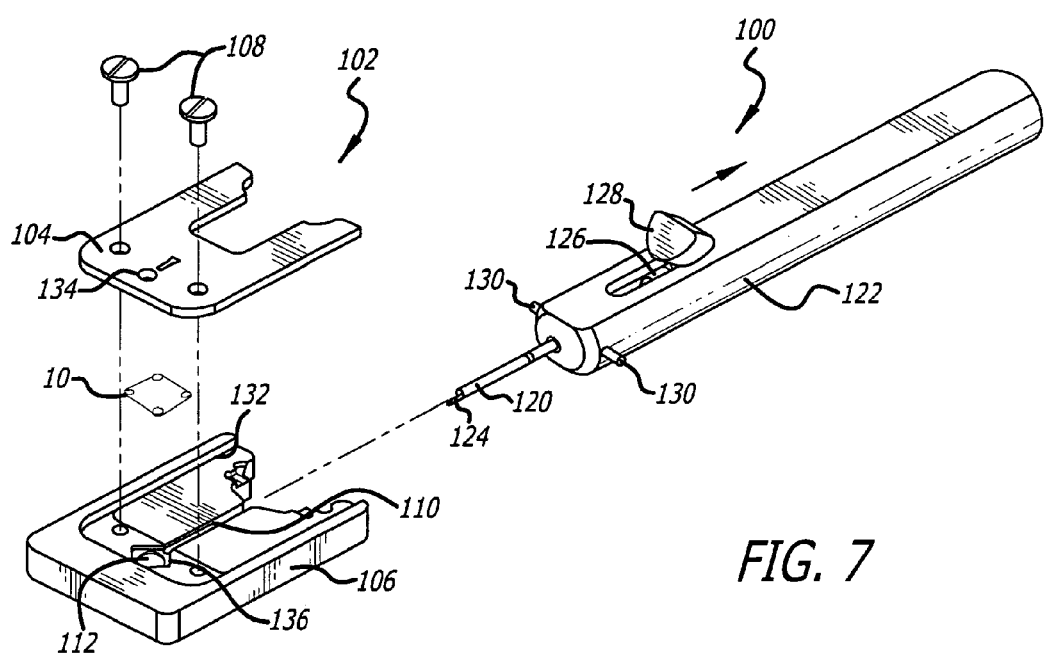
FIG. 7 is a perspective view of an injector and ring plate used to load and inject the ring.

FIG. 7 shows an embodiment of an injector 100 that can be used to inject a ring 10 into a patient's eye. The ring 10 can be loaded into the injector with the use of a ring plate 102. The ring plate 102 may include a cover 104 that is attached to a base plate 106 by fasteners 108. The base plate 106 has a channel 110 and a recess 112. The recess 112 receives the ring 10.

The injector 100 includes a cannula 120 attached to a handle 122. Within the cannula 120 is a wire hook 124. The wire hook 124 is connected to an inner slide tube 126 located within the handle 122. A button 128 is attached to the inner slide tube 126. The injector 100 may also have a pair of guide pins 130 that are attached to the handle 122 and cooperate with corresponding channel features 132 of the base plate 106 to properly align the injector 100 when the cannula 120 is inserted into the base plate channel 110.

In operation, the cannula 120 is inserted into the base plate channel 110. When fully inserted the wire hook 124 extends to approximately the center of the ring 10. The cover 104 may have an opening 134 that allows an operator to visually see the hook 124 within the ring opening. An operator then pulls the button 128 in the direction indicated by the arrow. Pulling the button 128 causes the hook 124 to grasp the ring loops and pull the ring 10 into the cannula 120. The recess 112 has tapered walls 136 to assist in the ring collapsing within the channel 112 for insertion into the cannula 120. Once loaded, the ring 10 can be injected into a patient's eye by pushing the button 128 in the opposite direction.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method of implanting, using an inserter, an iris-expanding medical device in an eye, wherein the inserter includes an inserter handle and a cannula attached to the inserter handle, the method comprising:
   retracting a slider of the inserter handle away from a holder of the iris-expanding medical device to cause the iris-expanding medical device to slide into a distal end of the cannula;
   removing the iris-expanding medical device and the distal end of the cannula from the holder;
   inserting the distal end of the cannula into the eye;
   moving the slider toward the cannula to eject the iris-expanding medical device from the distal end of the cannula toward an iris of the eye and to transition the iris-expanding medical device into an expanded configuration; and
   withdrawing the distal end of the cannula from the eye;
   wherein, in the expanded configuration, a first corner of the iris-expanding medical device is engaged with an edge portion of the iris and a second corner of the iris-expanding medical device is engaged with another edge portion of the iris.

2. The method of claim 1, wherein the iris-expanding medical device is collapsed into an insertion configuration in the distal end of the cannula.

3. The method of claim 1, wherein retracting the slider and removing the iris-expanding medical device from the holder occur simultaneously.

4. The method of claim 1, further comprising inserting the distal end of the cannula into the holder prior to retracting the slider.

5. The method of claim 1, wherein the iris-expanding medical device is positioned in a recess of the holder prior to retracting the slider.

6. The method of claim 1, further comprising grasping a hinge of the iris-expanding medical device to remove the iris-expanding medical device from the holder.

7. The method of claim 6, wherein the hinge of the iris-expanding medical device is grasped by a hook extending through the distal end of the cannula.

8. A method of implanting an iris-expanding medical device in an eye, the method comprising:
   sliding the iris-expanding medical device into a distal end of a cannula from a holder;
   inserting the distal end of the cannula into the eye;
   ejecting the iris-expanding medical device from the distal end of the cannula toward an iris of the eye, wherein the iris-expanding medical device is configured to expand following ejection;
   securing a first portion of the iris-expanding medical device to the iris of the eye; and
   securing a second portion of the iris-expanding medical device to the iris of the eye;
   wherein the iris-expanding medical device is positioned in a holder prior to sliding the iris-expanding medical device into the distal end of the cannula, and wherein the method further comprises inserting the distal end of the cannula into the holder.

9. The method of claim 8, further comprising grasping a third portion of the iris-expanding medical device with a hook prior to sliding the iris-expanding medical device into the distal end of the cannula.

10. The method of claim 8, further comprising securing a third portion of the iris-expanding medical device to the iris of the eye.

11. The method of claim 8, wherein the first portion of the iris-expanding device is secured to the iris before the second portion of the iris-expanding medical device.

* * * * *